US008852582B2

(12) United States Patent
Ansovini

(10) Patent No.: US 8,852,582 B2
(45) Date of Patent: Oct. 7, 2014

(54) COMPOSITIONS COMPRISING GLUTATHIONE REDUCTASE AND OXIDIZED GLUTATHIONE

(75) Inventor: Raffaele Ansovini, Perugia (IT)

(73) Assignees: Giulia Cattarini Mastelli, Genoa (IT); Laura Cattarini Mastelli, Taggia (IM) (IT); Raffaele Ansovini, Perugia (IT)

( * ) Notice: Subject to any disclaimer, the term of this patent is extended or adjusted under 35 U.S.C. 154(b) by 0 days.

(21) Appl. No.: 13/813,426

(22) PCT Filed: Jul. 29, 2011

(86) PCT No.: PCT/IB2011/053390
§ 371 (c)(1),
(2), (4) Date: Apr. 2, 2013

(87) PCT Pub. No.: WO2012/017367
PCT Pub. Date: Feb. 9, 2012

(65) Prior Publication Data
US 2013/0216514 A1     Aug. 22, 2013

(30) Foreign Application Priority Data
Aug. 2, 2010   (IT) .......................... MI2010A001459

(51) Int. Cl.
*A61K 38/44* (2006.01)
*C12Q 1/32* (2006.01)
*A61K 38/06* (2006.01)
*A61K 45/06* (2006.01)

(52) U.S. Cl.
CPC ............... *A61K 38/44* (2013.01); *A61K 38/063* (2013.01); *A61K 45/06* (2013.01); *C12Y 108/01007* (2013.01)
USPC ........................................... 424/94.4; 435/26

(58) Field of Classification Search
USPC ........................................... 435/26; 424/94.4
See application file for complete search history.

(56) References Cited

U.S. PATENT DOCUMENTS

| 5,281,353 | A * | 1/1994 | Park et al. .................. 510/114 |
| 6,251,857 | B1 | 6/2001 | Kozhemyakin et al. |
| 2004/0175358 | A1 | 9/2004 | Ansovini et al. |
| 2004/0223958 | A1 | 11/2004 | Ansovini |
| 2007/0270349 | A1 | 11/2007 | Benatti et al. |
| 2008/0221029 | A1 | 9/2008 | Day |
| 2011/0288161 | A1 | 11/2011 | Day |

FOREIGN PATENT DOCUMENTS

| CN | 1253832 A | 5/2000 |
| WO | 9809634 A1 | 3/1998 |
| WO | 9830228 A1 | 7/1998 |
| WO | 0071146 A2 | 11/2000 |
| WO | WO 02/76490 A1 * | 3/2002 |
| WO | 02062978 A1 | 8/2002 |
| WO | 2009023355 A2 | 2/2009 |

OTHER PUBLICATIONS

Davis, G. L. Treatment of Chronic Hepatitis C; British Medical Journal, vol. 323 (2001) pp. 141-142.*
Mylonakis et al. Plasma Viral Load Testing in the Management of HIV Infection; American Family Physician, vol. 63, No. 3 (2001) pp. 483-490.*
Shinazi et al. Cell-Based and Animal Models for Hepatitis B and C Viruses; Antiviral Chemistry and Chemotherapy, vol. 10 (1999) pp. 99-114.*
E. Garaci, A.T. Palamara, P. Di Francesco, C. Favalli, M.R. Ciriolo and G.Rotilio, Glutathione inhibits replication and expression of viral proteins in cultured cells infected with sendai virus, Biochemical and Biophysical Research Communications, Nov. 16, 1992, pp. 1090-1096, vol. 188, No. 3, Academic Press Inc., Orlando, DOI:10.1016/0006-291X(92)91343-O.
Vijayakumar Boggaram, Kerstin Larson and Bengt Mannervik, Characterization of Glutathione Reductase from Porcine Erythrocytes, Biochimica et Biophysica Acta, May 25, 1978, pp. 337-347, vol. 527, No. 2,1, Elsevier/North-Holland Biomedical Press, DOI:DOI:10.1016/0005-2744(78)90348-0.
Kenny K. Wong, Maria A. Vanoni and John S.Blanchard, Glutathione Reductase: Solvent Equilibrium and Kinetic Isotope Effects, Biochemistry, 1988, pp. 7091-7096, vol. 27, No. 18, American Chemical Society.
Donough J. O'Donovan, Julie P. Katkin, Toshiya Tamura, Charles V.Smith and Stephen E. Welty, Attenuation of Hyperoxia-Induced Growth Inhibition in H441 Cells by Gene Transfer of Mitochondrially Targeted Glutathione Reductase, American Journal of Respiratory Cell and Molecular Biology, Jun. 2000, pp. 732-738, vol. 22 No. 6, LNKD—PUBMED:10837371.
Mustafa Erat, Hülya Demir and Halis Şakiroğlu, Purification of Glutathione Reductase From Chicken Liver and Investigation of Kinetic Properties, Applied Biochemistry and Biotechnology. May 2005, pp. 127-138, vol. 125, No. 2 Humana Press Inc.
Anonymous, Glutathione Reductase Assay Kit, Catalog# 7510-100-K, 2008, pp. 1-7, Trevigen.

* cited by examiner

*Primary Examiner* — Susan Hanley
*Assistant Examiner* — Paul Martin
(74) *Attorney, Agent, or Firm* — Robert E. Alderson, Jr.

(57) ABSTRACT

Compositions comprising Glutathione Reductase (GSSG-r) and Oxidized Glutathione (GSSG) or pharmaceutically acceptable salts thereof for pharmaceutical use as antiviral and antibacterial agents and for the protection against the toxicity of free radicals and in particular radicals produced by the radiolysis of cellular water are provided. Methods of making and using such compositions are also provided.

9 Claims, 4 Drawing Sheets

Figure 1A

|   | 1  | 2      | 3           | 4           | 5           | 6         | 7         | 8         |
|---|----|--------|-------------|-------------|-------------|-----------|-----------|-----------|
| A | NC | NC+GR  | $10^{-9}$+GR | $10^{-9}$+GR | $10^{-9}$+GR | $10^{-9}$ | $10^{-9}$ | $10^{-9}$ |
| B | NC | NC+GR  | $10^{-8}$+GR | $10^{-8}$+GR | $10^{-8}$+GR | $10^{-8}$ | $10^{-8}$ | $10^{-8}$ |
| C | NC | NC+GR  | $10^{-7}$+GR | $10^{-7}$+GR | $10^{-7}$+GR | $10^{-7}$ | $10^{-7}$ | $10^{-7}$ |
| D | NC | NC+GR  | $10^{-6}$+GR | $10^{-6}$+GR | $10^{-6}$+GR | $10^{-6}$ | $10^{-6}$ | $10^{-6}$ |
| E | NC | NC+GR  | $10^{-5}$+GR | $10^{-5}$+GR | $10^{-5}$+GR | $10^{-5}$ | $10^{-5}$ | $10^{-5}$ |
| F | NC | NC+GR  | $10^{-4}$+GR | $10^{-4}$+GR | $10^{-4}$+GR | $10^{-4}$ | $10^{-4}$ | $10^{-4}$ |

Figure 1B

|            | Dilution ($Log_{10}$) | 24 Hours | 48 Hours | 72 Hours |
|------------|-----------------------|----------|----------|----------|
| NC         | NO                    | 0/6      | 0/6      | 0/6      |
| Polio      | -9                    | 0/3      | 0/3      | 3/3      |
| Polio      | -8                    | 0/3      | 3/3      | 3/3      |
| Polio      | -7                    | 0/3      | 3/3      | 3/3      |
| Polio      | -6                    | 4/4      | 4/4      | 4/4      |
| Polio      | -5                    | 4/4      | 4/4      | 4/4      |
| Polio      | -4                    | 3/3      | 3/3      | 3/3      |
| NC + GR    | NO                    | 0/6      | 0/6      | 0/6      |
| Polio + GR | -9                    | 0/3      | 0/3      | 0/3      |
| Polio + GR | -8                    | 0/3      | 0/3      | 0/3      |
| Polio + GR | -7                    | 0/3      | 0/3      | 0/3      |
| Polio + GR | -6                    | 0/2      | 0/2      | 0/2      |
| Polio + GR | -5                    | 2/2      | 2/2      | 2/2      |
| Polio + GR | -4                    | 3/3      | 3/3      | 3/3      |

Figure 2A

|   | 1 | 2 | 3 | 4 | 5 | 6 | 7 | 8 |
|---|---|---|---|---|---|---|---|---|
| A | NC | NC+GR | $10^{-5}$+GR | $10^{-5}$+GR | $10^{-5}$+GR | $10^{-5}$ | $10^{-5}$ | $10^{-5}$ |
| B | NC | NC+GR | $10^{-4}$+GR | $10^{-4}$+GR | $10^{-4}$+GR | $10^{-4}$ | $10^{-4}$ | $10^{-4}$ |
| C | NC | NC+GR | $10^{-3}$+GR | $10^{-3}$+GR | $10^{-3}$+GR | $10^{-3}$ | $10^{-3}$ | $10^{-3}$ |
| D | NC | NC+GR | $10^{-2}$+GR | $10^{-2}$+GR | $10^{-2}$+GR | $10^{-2}$ | $10^{-2}$ | $10^{-2}$ |
| E | NC | NC+GR | $10^{-1}$+GR | $10^{-1}$+GR | $10^{-1}$+GR | $10^{-1}$ | $10^{-1}$ | $10^{-1}$ |
| F | NC | NC+GR | $10^{0}$+GR | $10^{0}$+GR | $10^{0}$+GR | $10^{0}$ | $10^{0}$ | $10^{0}$ |

Figure 2B

|   | Dilution (Log$_{10}$) | 24 Hours | 48 Hours | 72 Hours |
|---|---|---|---|---|
| NC | NO | 0/6 | 0/6 | 0/6 |
| HSV-2 | -5 | 0/3 | 0/3 | 0/3 |
| HSV-2 | -4 | 0/3 | 0/3 | 0/3 |
| HSV-2 | -3 | 0/3 | 0/3 | 0/3 |
| HSV-2 | -2 | 0/3 | 2/3 | 3/3 |
| HSV-2 | -1 | 3/3 | 3/3 | 3/3 |
| HSV-2 | 0 | 3/3 | 3/3 | 3/3 |
| NC + GR | NO | 0/6 | 0/6 | 0/6 |
| HSV-2 + GR | -5 | 0/3 | 0/3 | 0/3 |
| HSV-2 + GR | -4 | 0/3 | 0/3 | 0/3 |
| HSV-2 + GR | -3 | 0/3 | 0/3 | 0/3 |
| HSV-2 + GR | -2 | 0/3 | 0/3 | 0/3 |
| HSV-2 + GR | -1 | 0/3 | 0/3 | 0/3 |
| HSV-2 + GR | 0 | 3/3 | 3/3 | 3/3 |

Figure 3A

|   | 1  | 2     | 3             | 4             | 5           | 6           | 7          | 8          |
|---|----|-------|---------------|---------------|-------------|-------------|------------|------------|
| A | NC | NC+GR | $10^{-11}$+GR | $10^{-11}$+GR | $10^{-5}$+GR | $10^{-5}$+GR | $10^{-12}$ | $10^{-12}$ |
| B | NC | NC+GR | $10^{-10}$+GR | $10^{-10}$+GR | $10^{-4}$+GR | $10^{-4}$+GR | $10^{-11}$ | $10^{-11}$ |
| C | NC | NC+GR | $10^{-9}$+GR  | $10^{-9}$+GR  | NC          | NC          | $10^{-10}$ | $10^{-10}$ |
| D | NC | NC+GR | $10^{-8}$+GR  | $10^{-8}$+GR  | NC          | NC          | $10^{-9}$  | $10^{-9}$  |
| E | NC | NC+GR | $10^{-7}$+GR  | $10^{-7}$+GR  | $10^{-4}$   | $10^{-4}$   | $10^{-8}$  | $10^{-8}$  |
| F | NC | NC+GR | $10^{-6}$+GR  | $10^{-6}$+GR  | $10^{-5}$   | $10^{-5}$   | $10^{-7}$  | $10^{-7}$  |

Figure 3B

|           | Dilution (Log$_{10}$) | 14 Days | 17 Days | 23 Days |
|-----------|-----------------------|---------|---------|---------|
| NC        | NO                    | 0/6     | 0/6     | 0/6     |
| SV40      | -12                   | 0/2     | 0/2     | 0/2     |
| SV40      | -11                   | 0/2     | 0/2     | 0/2     |
| SV40      | -10                   | 0/2     | 0/2     | 0/2     |
| SV40      | -9                    | 0/2     | 0/2     | 0/2     |
| SV40      | -8                    | 0/2     | 1/2     | 1/2     |
| SV40      | -7                    | 2/2     | 2/2     | 2/2     |
| SV40      | -6                    | 2/2     | 2/2     | 2/2     |
| SV40      | -4                    | 2/2     | 2/2     | 2/2     |
| NC + GR   | NO                    | 0/6     | 0/6     | 0/6     |
| SV40 + GR | -11                   | 0/2     | 0/2     | 0/2     |
| SV40 + GR | -10                   | 0/2     | 0/2     | 0/2     |
| SV40 + GR | -9                    | 0/2     | 0/2     | 0/2     |
| SV40 + GR | -8                    | 0/2     | 0/2     | 0/2     |
| SV40 + GR | -7                    | 0/2     | 0/2     | 0/2     |
| SV40 + GR | -6                    | 0/2     | 2/2     | 2/2     |
| SV40 + GR | -5                    | 0/2     | 2/2     | 2/2     |
| SV40 + GR | -4                    | 0/2     | 2/2     | 2/2     |

Figure 4A

|   | 1 | 2 | 3 | 4 | 5 | 6 | 7 | 8 |
|---|---|---|---|---|---|---|---|---|
| A | NC | NC+GR | $10^{-5}$+GR | $10^{-5}$+GR | $10^{-5}$+GR | $10^{-5}$ | $10^{-5}$ | $10^{-5}$ |
| B | NC | NC+GR | $10^{-4}$+GR | $10^{-4}$+GR | $10^{-4}$+GR | $10^{-4}$ | $10^{-4}$ | $10^{-4}$ |
| C | NC | NC+GR | $10^{-3}$+GR | $10^{-3}$+GR | $10^{-3}$+GR | $10^{-3}$ | $10^{-3}$ | $10^{-3}$ |
| D | NC | NC+GR | $10^{-2}$+GR | $10^{-2}$+GR | $10^{-2}$+GR | $10^{-2}$ | $10^{-2}$ | $10^{-2}$ |
| E | NC | NC+GR | $10^{-1}$+GR | $10^{-1}$+GR | $10^{-1}$+GR | $10^{-1}$ | $10^{-1}$ | $10^{-1}$ |
| F | NC | NC+GR | NC | NC | NC | NC | NC | NC |

Figure 4B

| Dilution | MuLV | | MuLV + GR 0.67% | | | |
|---|---|---|---|---|---|---|
| Log10 | Inoculum | Infective | 30 min | Reduction | 180 min | reduction |
| 0 | 100,000 | 47,400,000 | NT | - | 75,000 | 632 |
| -1 | 10,000 | 1,900,000 | 5,870 | 323 | 6,500 | 292 |
| -2 | 1,000 | 475,000 | NEG | - | NEG | - |
| -3 | 100 | 23,200 | NEG | - | NEG | - |
| -4 | 10 | 4,330 | NEG | - | NEG | - |
| -5 | 0 | NEG | NEG | - | NEG | - |

COMPOSITIONS COMPRISING GLUTATHIONE REDUCTASE AND OXIDIZED GLUTATHIONE

CROSS-REFERENCE TO RELATED APPLICATIONS

This application is a National Phase Application of PCT International Application No. PCT/IB2011/053390, International Filing Date, Jul. 29, 2011, claiming priority to Italian Patent Application No. MI2010A001459, filed Aug. 2, 2010, both of which are hereby incorporated by reference in their entirety.

FIELD OF THE INVENTION

A composition comprising Glutathione Reductase (GSSG-r) and Oxidized Glutathione (GSSG) or pharmaceutically acceptable salts thereof for pharmaceutical use as antiviral and antibacterial agents and for the protection against the toxicity of the free radicals and in particular of the radicals produced by the radiolysis of cellular water is an object of the present invention.

BACKGROUND OF THE INVENTION

The therapy of viral pathologies currently uses chemotherapy agents with multiple action mechanisms. In particular, considering flu as a typical viral disease, there are used M2 inhibitors such as Amantadine and neuraminidase inhibitors, such as Oseltamivir and Zanamivir. It is known that the virus are capable of acquiring resistance against antiviral agents, hence there strongly arises the need of therapies alternative to those using antiviral agents, also due to the fact that use of these compounds, especially Amantadine, is often associated to severe adverse effects and thus it is not recommended unless under particular conditions.

In addition, there are several viruses that are not currently covered by efficient antiviral therapies. By way of example, currently there are no therapies capable of fighting Poliovirus. The people intensive migrations that occur nowadays have also spread viral strains typical of some areas of the world to areas where the same were unknown, in other cases they have brought back problems related to viral strains that had been considered eliminated in that specific area. Thus, there strongly arises the need of having efficient therapies and with wide coverage against virus.

Glutathione is present in cells in form of Reduced Glutathione GSH and Oxidized Glutathione GSSG. The GSH:GSSG ratio indicates the antioxidant capacity of the cell. Said ratio is maintained in favour of GSH due to GSSG-r, an enzyme belonging to the class of oxidoreductase, which regenerates GSH starting from GSSG, by transferring electrons transferred from the NADPH cofactor, a derivative of vitamin PP (nicotinic acid). Maintaining a correct GSH:GSSG ratio is an essential requirement for the vitality and wellbeing of the cell. A misbalanced GSH:GSSG ratio was observed in numerous pathologic conditions, for example in viral infections, tumours, cystic fibrosis, neurodegenerative diseases. In said pathologic conditions there arises a misbalance in the GSH:GSSG ratio, which is displaced in favour of GSSG hence the cell loses the oxide-reductive balance thereof.

Administration of GSH was proposed in order to counter such loss of balance. Actually, GSH is the most known and powerful physiological antioxidant, and thus already used as a supplement in anti-aging therapies, and it was surprisingly proven to have antiviral activity (Garaci et al., 1992). The supplementation of GSH however proved to be complex, in that it is poorly absorbed in the gastrointestinal tract. This drawback was overcome by administering GSH precursors, such as S-adenosyl-1-methionine (SAMe) and/or N-acetylcysteine (NAC).

WO/2005/063795 describes the use of GSH derivatives for treating Paramyxovirus, Orthomyxovirus, Herpes Simplex Virus and HIV infections.

WO00/71146 describes the use of GSSG-r in the HIV therapy.

WO/2002/083168 describes a combination of two enzymes: GSSG-r and Glutathione peroxidase (GSH-px) as adjuvants in the therapy with Interferons.

As of date, there has been no indication as regards the therapeutic use of GSSG.

SUMMARY OF THE INVENTION

An entirely new and surprising approach is that claimed in the present invention, which proposes a formulation that is active and safe in the treatment and prophylaxis of viral diseases and, more generally, in the reduction of cellular damage caused by the loss of the oxide-reductive balance of the cell, for example in the protection of the toxicity of the produced radicals which derive from the radiolysis of cellular water. Said composition, as more apparent from the description, from the examples and from the claims that follow and which form an integral part of the present application, has remarkable and surprising wide spectrum antiviral properties.

BRIEF DESCRIPTION OF THE FIGURES

FIG. 1, Poliovirus 3
A: shows a micro-plate and the treatment to which each and every well was subjected. The exponents refer to the logarithmic dilution of the Poliovirus 3. NC=negative control. GR=treated.
B: anti-poliovirus 3 activity.
FIG. 2, Herpes simplex 2
A: shows a micro-plate and the treatment to which each and every well was subjected. The exponents refer to the logarithmic dilution of Herpes simplex 2. NC=negative control. GR=treated.
B: anti-herpes simplex 2 activity.
FIG. 3, Polyomavirus SV40
A: shows a micro-plate and the treatment to which each and every well was subjected. The exponents refer to the logarithmic dilution of Polyomavirus SV40. NC=negative control. GR=treated.
B: anti-polyomavirus SV40 activity.
FIG. 4, Murine Laeukemia Virus
A: shows a micro-plate and the treatment to which each and every well was subjected. The exponents refer to the logarithmic dilution of MuLK. NC=negative control. GR=treated.
B: anti-MuLV activity.

The present invention regards a composition comprising GSSG-r and GSSG or pharmaceutically acceptable salts thereof for pharmaceutical use as antiviral or antibacterial agents and, more generally, at reducing the cellular damage caused by the loss of the oxide-reductive balance of the cell, such as for example when the cellular environment loses the oxide-reductive balance (reduction of the GSH/GSSG ratio) thereof due to an intracellular viral infection and in the protection of the toxicity of the radicals produced by the radiolysis of cellular water.

Regarding the present invention, GSH (reduced glutathione) refers to a tripeptide having the L-Glu-L-Cys-Gly structure, while oxidized Glutathione GSSG refers to a dipeptide in which two molecules of GSH are bonded to each other through a disulphide bond.

A particularly important aspect lies in the fact that said composition has a wide spectrum activity, being efficient towards RNA or DNA virus, with or without viral envelope, retrovirus and bacteria, at non-cytotoxic concentrations.

Preparation and Storage of the GSSGr+GSSG Formulation

The composition of the present invention comprises GSSG-r and GSSG or a pharmaceutically acceptable salt thereof, combined together for example according to the method claimed herein. The starting GSSG-r can be lyophilized GSSG-r, obtained from human erythrocytes, GSSGr in suspension with ammonium sulphate or recombinant human GSSG-r. In a further embodiment, GSSG-r is conjugated with pharmaceutically acceptable molecules, for example pegylated GSSG-r is used.

GSSG can be obtained through any of the conventional methods used for preparation thereof. For example, GSSG can be obtained by chemical synthesis through the procedure described in Bull. Chem. Soc. Jpn., 53, 2529, 1980.

Examples of pharmaceutically acceptable salts of GSSG in form of water soluble, fat soluble or dispersible products comprise non-toxic salts of inorganic acids, organic acids or bases, and quaternary ammonium salts or the like. Examples of such inorganic or organic acids include acetate, adipate, arginate, aspartate, benzoate, benzenesulfonate, bisulphate, butyrate, citrate, camphorate, camphorsulfonate, cyclopentylpropionate, digluconate, dodecyl sulphate, ethanesulfonate, fumarate, glucoheptonate, glycerophosphate, hemisulphate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulphate, 3-phenylpropionate, piclate, pivalate, propionate, succinate, tartrate, thiocyanate, tosylate, undecanoate and the like. Examples of base salts include alkaline metal salts, such as ammonium, sodium, potassium, earth-alkaline metal salts, such as calcium and magnesium salts, organic base salts, dicyclohexylamine and N-methyl-D-glucamine salts, and salts with amino acids such as arginine, lysine and analogues thereof.

In case of use of GSSG-r in suspension with ammonium sulphate, it is recommendable to eliminate ammonium sulphate due to the toxicity thereof.

Ammonium sulphate can be eliminated for example through dialysis.

Subsequently, an aliquot of the suspension of GSSG-r without the ammonium sulphate to which powder GSSG is added is taken. The GSSG-r and GSSG composition is for example maintained under stirring at 37° C. for a period of time comprised between 30 minutes and 3 hours, preferably for 1 hour. Alternatively, it can be conducted at ambient temperature or at a temperature range between ambient temperature and 42° C.

The preparation is thus ready for use. When storage for long periods of time, the preparation is stored at temperatures below −20° C. in aliquots, preferably at −37° C. During use, the aliquot is kept under stirring at a temperature comprised between ambient temperature and 42° C., for example at 37° C. for a period of time comprised between 30 minutes and 3 hours, preferably for 1 hour.

The composition of the invention is obtained by adding GSSG powder to the suspension of GSSG-r in a variable weight/volume ratio comprised between 1:4 and 1:1, preferably between 1:2.5 and 1:1.5, wherein the suspension of the starting GSSG-r contains a minimum of 100 Enzymatic units/ml.

In particular, the weight$_{GSSG}$/UE$_{GSSG-r}$/ml ratio, wherein UE$_{GSSG-r}$/ml are the enzymatic units of Glutathione Reductase per ml of solution, will be comprised between 1:100 and 1:3600, preferably between 1:400 and 1:2000, more preferably between 1:600 and 1:1000.

The components are mixed as described above, so as to obtain the desired GSSG-r/GSSG complex. In a preferred embodiment, said composition comprises 0.500 mg of GSSG and at least 100 Units of GSSG-r per 1 ml.

The expression functional unit is used to describe an aliquot of 4 ml of the composition prepared as described, comprising about 2 mg of GSSG and at least 400 Units of GSSGr.

The composition claimed herein is efficient at reducing the cellular damage caused by the loss of the oxide-reductive balance of the cell, for example in the protection from the toxicity of the radicals produced by the radiolysis of cellular water as well as in the treatment and prevention of viral diseases.

The observed effect is entirely unexpected and surprising, given that there occurs a restoration of the oxide-reductive balance of the cell due to the administration, in combination with the GSSG9r enzyme, of Glutathione in oxidised form, and not Glutathione in reduced form, which is the species present in defect in the cell in the described stress condition.

The composition according to the present invention can be formulated for oral, buccal, parenteral, intravenous, rectal, intravaginal or transdermic administration or in a form suitable for administration through inhalation or insufflation (both buccal or nasal).

For oral administration, the pharmaceutical compositions can be found, for example, in form of tablets or capsules prepared conventionally starting from the composition at the dry state, with pharmaceutically acceptable excipients such as bonding agents (for example pregelatinized maize starch, polyvinylpyrrolidone or hydroxypropyl methylcellulose); filler agents (such as for example lactose, microcrystalline cellulose or calcium hydrogen phosphate); lubricants (for example magnesium stearate, talcum or silica); disintegrants (for example potato starch or sodium starch glycolate); or inhibitor agents (for example sodium lauryl sulphate). The tablets can be coated using the methods well known in the art. The liquid preparations for oral administration may for example be in form of solutions, syrups or suspensions or they can be lyophilized products to be reconstituted, before use, using water or other suitable carriers. Such liquid preparations can be prepared through conventional methods using pharmaceutically acceptable additives such as suspension agents (for example sorbitol syrup, cellulose derivatives or edible hydrogenated fats); emulsifying agents (for example lecithin or acacia); non-aqueous carriers (for example almond oil, oil esters, ethyl alcohol or fractionated vegetable oils); and preservatives (for example methyl- or propyl-p-hydroxybenzoate or sorbic acid). The preparation may suitably contain flavours, colouring agents and sweeteners.

The preparations for oral administration can be suitably formulated to allow the controlled release of the active ingredient.

For buccal administration, the compositions may be in form of tablets or pills formulated conventionally, suitable for absorption at the buccal mucosa level. Typical buccal formulations are tablets for sublingual administration.

The compounds according to the present invention can be formulated for a parenteral administration through subcutaneous, intramuscular, intravenous or intra-arterial injection.

The formulations for injection may be in form of a single dose for example a vial, with or without added preservatives or in prefilled syringes. The compositions may be in such form as suspensions, solutions or emulsions in oily or aqueous carriers and they may contain agents formulated as suspension, stabilisers and/or dispersants. Alternatively, the active ingredient may be in form of powder to be reconstituted, before use, using a suitable carrier, for example sterile water.

According to the present invention, the compounds can also be formulated to form rectal or vaginal compositions such as suppositories or retention enema, for example containing the base components of the common suppositories such as cocoa butter or other glycerides or in ovules or intra vaginal creams.

Additionally to the previously described compositions, the compounds can also be formulated as depot preparations. Such extended action formulations can be administered by implantation (ad for example subcutaneous, transcutaneous or intramuscular implantation) or through intramuscular injection. Thus, for example, the compounds, according to the present invention, can be formulated using suitable polymer or hydrophobic material (for example in form of an emulsion in a suitable oil) or ion exchange resins or as a minimally soluble derivative, for example minimally soluble salt.

Preferred examples of pharmaceutical preparations of the composition claimed herein include an oral preparation, a nasal or oral aerosol, an inhalant, an ointment, drops, suppositories or formulations for the intravenous or intramuscular administration.

Said formulations can be prepared according to conventional methods, such as those described in Remington's Pharmaceutical Sciences Handbook, Mack Pub. Co., N.Y., USA, 17th edition, 1985.

Therapeutic Dosage

According to the present invention the dose of the composition of the invention proposed for administration to a man (with body weight of about 70 Kg) ranges from 0.1 mg to 2 g and preferably from 1 mg to 100 mg of the composition per dose unit. The dose unit can be administered, for example, from 1 to 4 times a day. The dose will depend on the selected method of administration. It should be considered that it could be required to continuously vary the dose depending on the age and weight of the patient and also the seriousness of the clinical condition to be treated. Lastly, the exact dose and method of administration will be at the discretion of the doctor or veterinarian.

The formulation is administered for example through intravenous administration. In this case, the functional units will be prepared as injectable formulations.

Alternatively, the same therapeutic pattern may be applied by administering said functional units in the various pharmaceutical forms.

EXAMPLES

Example 1

Antiviral Activity against the Flu Virus of a Composition Comprising GSSG-r and GSSG in Balb/C Mice Two-month old Balb/C mice were used for conducting the experiment. The mice, anaesthetised, were infected—through aerosol—with a swine flu strain adapted to the mouse, A/SW/Finistere/2899/82. The animals are treated with the formulation in question through intranasal method.

Experimental Groups:

Group 1: infected and treated with GSSG-r+GSSG 3 times a day, every 4 hours for 4 days.

Group 2: infected, not treated.

Group 3: infected and treated with saline solution 3 times a day, every 4 hours for 4 days.

Within 5 days from the infection, the number of dead animals with respect to the number of animals that survived in the various groups was as follows:

Group 1: 3/10
Group 2: 8/10
Group 3: 9/10

The results show that the formulation comprising GSSG-r+GSSG is capable of considerably reducing the lethality observed in the model of experimental flu.

Example 2

Antiviral Activity against the Poliovirus 3 of a Composition Comprising GSSG-r And GSSG In VERO Cells VERO cells are a cellular line derived from renal epithelial cells of chimpanzees. Said VERO cells were plated in 48-well micro-plates, in DMEM (Dulbecco's Modified Eagle Medium) culture medium at 10% of FCS (Foetal Cow Serum), $5\times10^4$ cells/well in 0.5 ml. One plate, which was incubated at 37° C., 5% $CO_2$ was prepared. The state of growth of the cells in the wells and the percentage of confluence, which was of about 90%, was checked after two days. The culture medium was suctioned and, as illustrated in the scheme indicated in FIG. 1A, 100 μl of the scalar dilutions from $10^{-4}$ to $10^{-9}$ of Poliovirus 3—an RNA virus without viral envelope—were added into the wells.

Subsequently the GSSG-r/GSSG composition, comprising at least 100 units of GSSG-r and 2 mg of GSSG/ml, was added diluting it to 0.67% in the wells indicated with GR in FIG. 1A. DMEM culture medium at 2% of FCS was added in all wells to obtain a final volume of 0.5 ml per well. The micro-plate was incubated at 37° C., 5% $CO_2$. The Poliovirus 3 load was determined after three days of incubation evaluating the cytopathic effect induced by the virus. The formulation did not reveal any cytotoxic activity, while it showed an antiviral activity against Poliovirus 3 with a reduction of the viral load by 4 logarithms (FIG. 1B).

Example 3

Antiviral Activity against Virus Herpes Simplex 2 of a Composition Comprising GSSG-r and GSSG in VERO Cells VERO cells were plated in 48-well micro-plates, in DMEM culture medium at 10% of FCS, $5\times10^4$ cells/well in 0.5 ml. One plate, which was incubated at 37° C., 5% $CO_2$, was prepared. The state of growth of the cells in the wells and the percentage of confluence, which was of about 90%, was checked after two days. The culture medium was suctioned from all plates and, as illustrated in FIG. 2A, 100 μl of the scalar dilutions from 100 to $10^{-5}$ of Herpes simplex 2 virus—an RNA virus without viral envelope—were added into the wells. Subsequently, the GSSG-r/GSSG composition, comprising at least 100 units of GSSG-r and 2 mg of GSSG/ml, was added in the wells indicated with GR in FIG. 2A obtaining a final concentration of 0.67%. DMEM culture medium at 2% of FCS was added in all wells to obtain a final volume of 0.5 ml per well. The micro-plate was incubated at 37° C., 5%

$CO_2$. The Herpes simplex 2 virus load was determined after three days of incubation evaluating the occurrence of the cytopathic effect induced by the virus. The load was $1\times10^3$ virus units/ml. The formulation did not reveal any cytotoxic activity, while it showed an antiviral activity against the Herpes simplex 2 virus with a reduction of the viral load by 2 logarithms (FIG. 2B).

Example 4

Antiviral Activity against Polyomavirus SV40 of a Composition Comprising GSSG-r and GSSG in VERO Cells VERO cells were plated in 48-well micro-plates, in DMEM culture medium at 10% of FCS, $5\times10^4$ cells/well in 0.5 ml. One plate, which was incubated at 37° C., 5% $CO_2$ was prepared. The state of growth of the cells in the wells and the percentage of confluence, which was of about 90%, was checked after two days. The culture medium was suctioned from all plates and, as illustrated in FIG. 3A, 100 μl of the scalar dilutions from $10^{-4}$ to $10^{-11}$ of Polyomavirus SV40—a DNA virus without viral envelope—were added into the wells. The viral adsorption was carried out at ambient temperature by positioning the micro-plate on a stirrer for 2 hours.

After washing with PBS, the composition comprising at least 100 units of GSSG-r and 2 mg of GSSG/ml was added to the final concentration of 0.67% in the wells indicated with GR in FIG. 3A. DMEM culture medium at 2% of FCS was added in all wells to obtain a final volume of 0.5 ml per well. The micro-plate was incubated at 37° C., 5% $CO_2$. The Polyomavirus SV40 load was determined after three weeks of incubation by evaluating the occurrence of transformation foci caused by the virus. The load was $1\times10^{7.5}$ virus units/ml. The formulation did not reveal any cytotoxic activity, while it showed an antiviral activity against Polyomavirus SV40 with a reduction of the viral load by 1.5 logarithms. The effect of said formulation was also observed on the occurrence of the viral cytopathic effect, which was delayed by 24 hours on all dilutions (FIG. 3B).

Example 5

Antiviral Activity against Murine Leukaemia Virus (MuLV) of a Composition Comprising GSSG-r and GSSG in Mink Lung Cells Mink Lung cells were plated in 48-well micro-plates, in DMEM culture medium at 10% of FCS, $5\times10^4$ cells/well in 0.5 ml. One plate, which was incubated at 37° C., 5% $CO_2$ was prepared. The state of growth of the cells in the wells and the percentage of confluence, which was of about 90%, was checked after one day. The culture medium was suctioned from all plates and, as illustrated in FIG. 3A, 100 μl of the scalar dilutions from $10^{-1}$ to $10^{-5}$ of the MuLV—an RNA virus with viral envelope—were added into the wells. Viral adsorption was conducted by incubating the plate at 37° C., 5% $CO_2$ for 30 minutes. After washing with PBS the composition comprising at least 100 units of GSSG-r and 2 mg of GSSG/ml was added at the final concentration of 0.67% in the wells indicated with GR in FIG. 3A. In particular, the treatment was conducted in a series of wells 30 minutes after the viral infection and, in another series of wells, the same treatment was conducted 180 minutes after the viral infection. DMEM culture medium at 2% of FCS was added in all wells to obtain a final volume of 0.5 ml per well. The micro-plate was incubated at 37° C., 5% $CO_2$. The MuLV load was determined after 4 days of incubation collecting the supernatant and conducting the titration of the genomic RNA of MuLV. The load was equivalent to $1\times10^{7.5}$ virus units/ml. The treatment with the composition comprising GSSG and GSSG-r did not reveal any cytotoxic activity, while antiviral activity against MuLV was observed. The viral replication was entirely inhibited up to inoculums at concentrations equivalent to $10^4$. Infections with greater concentrations of MuLV revealed an inhibition of the viral replication. In cases where said composition was added 180 minutes instead of 30 minutes after viral infection, it still revealed to be active, though less efficient (FIG. 4B).

The invention claimed is:

1. A method for treating or ameliorating viral infections comprising: administering a composition which comprises Glutathione Reductase GSSG-r and Oxidized Glutathione GSSG or pharmaceutically acceptable salts thereof to a subject in need thereof, wherein said viral infections are caused by a virus selected from the group consisting of: flu virus, Poliovirus 3, Herpes Simplex Virus 2, Polyomavirus SV40, and Murine Leukaemia Virus MuLV.

2. The method of claim 1, wherein said method reduces cell damage caused by the loss of the oxide-reductive balance of the cell and protects against the toxicity of radicals produced by the radiolysis of cellular water.

3. The method of claim 1 wherein GSSG and GSSG-r are present in a weight/volume ratio between about 1:4 and about 1:1 and wherein said GSSG-r is present at a minimum of 100 Enzymatic units/ml.

4. The method of claim 3 wherein GSSG and a suspension of GSSG-r are present in a 1:2 weight/volume ratio.

5. The method of claim 3 wherein 1 ml comprises about 0.500 mg of GSSG and at least 100 Units of GSSG-r.

6. The method of claim 3, wherein a functional unit of said composition comprises at least 400 Units of GSSG-r about 2 mg of GSSG and comprises an aliquot of about 4 ml comprising said composition.

7. The method of claim 1, wherein the weight ratio of GSSG/UEGSSGr/ml comprises between about 1:100 and about 1:3600, wherein the amount of UEGSSG-r/ml is expressed as enzymatic units of Glutathione Reductase per ml of solution.

8. The method of claim 1 wherein the composition is in the form of a pharmaceutical preparation.

9. The method of claim 1, wherein said composition is in a form selected from the group consisting of: oral preparations, nasal or oral aerosols, inhalants, ointments, drops, suppositories, ovules, intimate creams and formulations for intravenous, intramuscular or subcutaneous administration.

* * * * *